United States Patent
Simon

(10) Patent No.: US 8,044,359 B2
(45) Date of Patent: Oct. 25, 2011

(54) THREE DIMENSIONAL DOSIMETRY USING SOLID ARRAY GEOMETRY

(75) Inventor: William E. Simon, Melbourne, FL (US)

(73) Assignee: SunNuclear Corp., Melbourne, FL (US)

( * ) Notice: Subject to any disclaimer, the term of this patent is extended or adjusted under 35 U.S.C. 154(b) by 113 days.

(21) Appl. No.: 12/401,949

(22) Filed: Mar. 11, 2009

(65) Prior Publication Data

US 2009/0250618 A1 Oct. 8, 2009

Related U.S. Application Data

(60) Provisional application No. 61/035,834, filed on Mar. 12, 2008.

(51) Int. Cl.
*G01T 1/02* (2006.01)
(52) U.S. Cl. .................... 250/370.07; 378/207
(58) Field of Classification Search .............. 378/207; 250/370.07
See application file for complete search history.

(56) References Cited

U.S. PATENT DOCUMENTS

| | | | |
|---|---|---|---|
| 4,613,754 A * | 9/1986 | Vinegar et al. | 250/252.1 |
| 5,262,649 A * | 11/1993 | Antonuk et al. | 250/370.09 |
| 5,635,709 A | 6/1997 | Sliski et al. | |
| 5,661,310 A | 8/1997 | Jones | |
| 6,398,710 B1 | 6/2002 | Ishikawa et al. | |
| 6,594,336 B2 | 7/2003 | Nishizawa et al. | |
| 6,788,759 B2 | 9/2004 | Op De Beek et al. | |
| 6,904,162 B2 | 6/2005 | Robar et al. | |
| 6,974,254 B2 | 12/2005 | Paliwal et al. | |
| 7,098,463 B2 | 8/2006 | Adamovics | |
| 7,116,749 B2 | 10/2006 | Besson | |
| 7,233,688 B2 | 6/2007 | Ritt et al. | |
| 7,349,523 B2 * | 3/2008 | Jenkins et al. | 378/65 |
| 7,352,840 B1 | 4/2008 | Nagarkar et al. | |
| 7,371,007 B2 | 5/2008 | Nilsson | |
| 7,471,765 B2 | 12/2008 | Jaffray et al. | |
| 2002/0080912 A1 | 6/2002 | Mackie et al. | |
| 2003/0043960 A1 | 3/2003 | Op De Beek et al. | |
| 2004/0120560 A1 | 6/2004 | Robar et al. | |
| 2004/0211917 A1 | 10/2004 | Adamovics | |
| 2004/0228435 A1 | 11/2004 | Russell | |
| 2004/0251419 A1 | 12/2004 | Nelson et al. | |
| 2005/0013406 A1 | 1/2005 | Dyk et al. | |
| 2006/0002519 A1 * | 1/2006 | Jenkins et al. | 378/207 |
| 2007/0195930 A1 | 8/2007 | Kapatoes et al. | |
| 2008/0049898 A1 | 2/2008 | Romesberg, III et al. | |
| 2009/0003512 A1 | 1/2009 | Pouliot et al. | |

* cited by examiner

*Primary Examiner* — Constantine Hannaher
(74) *Attorney, Agent, or Firm* — Allen, Dyer, Doppelt, Milbrath & Gilchrist, P.A.

(57) ABSTRACT

A dosimeter comprising an ionizing radiation detector array is used to generally encompass a three dimensional geometric shape such as that employed as a phantom in radiation dosimetry measurements. The ionizing radiation detector array may include passive or active detectors. The active detectors in the array may comprise diodes, ionization chambers, luminescent sensors or amorphous silicon. The three dimensional geometric shape may comprise a shape defined by a closed directrix, wherein each of a plurality of detectors within the ionizing detector array is within an envelope defined by a generatrix of the directrix. The closed directrix may be an open or closed cylinder, or a structure having a cross section described by a polygon. The plurality of detectors may only be positioned on or at least proximate the envelope.

34 Claims, 7 Drawing Sheets

REGULAR PENTAGON

IRREGULAR PENTAGON

CONVEX OCTAGON

CONCAVE OCTAGON

THREE DIMENSIONAL DOSIMETRY USING SOLID ARRAY GEOMETRY

CROSS REFERENCE TO RELATED APPLICATIONS

This application incorporates by reference and claims priority to application Ser. No. 61/035,834 filed Mar. 12, 2008 for "Three Dimensional Dosimetry Using Solid Array Geometry," and commonly owned.

FIELD OF INVENTION

The invention generally relates to radiation measurement equipment for radiation therapy and treatment, and in particular to systems and methods for measuring and localizing, spatially and/or temporally, a dose in a phantom for supporting quality assurance (QA) in radiation therapy beam delivery.

BACKGROUND

There is a need for an accurate measurement of dose in a stationary object that simulates a patient, the stationary object herein referred to and well known as a phantom, while a radiation therapy delivery system moves with respect to the phantom, and that such a measurement results in a three dimensional (3-D) dose map that is coherent at any beam angle relative to the phantom. By coherent, it is meant that there is consistency with respect to a time and across time, with an inference to a geometrical projection (or property) of a detector array measurement that remains consistent as a radiation source moves relative to the detector array. A more detailed discussion of measurement coherence is addressed later in this document. Traditional or conventional radiation therapy delivery techniques have used treatment fields, where the beam axis remains stationary while the beam is on. This is true for the historical blocked fields of Cobalt and linear accelerator (LINAC) systems, and the more recent intensity modulated radiation therapy (IMRT) fields. Quality assurance (QA) methods have incorporated film, a passive array, and electronic active detector arrays (such as MapCHECK™, MatriXX™, and Seven29™)[1], which provide two dimensional (2-D) planes orthogonal to the beam axis and result in a 2-D dose map of the field. With the evolution of delivery techniques where the source rotates (or moves) while the patient remains stationary (such as Rapid Arc™, HI-ART™, VMAT™, Single Arc Therapy™ (SAT), CyberKnife™, and Renaissance™)[2], the 2-D array no longer provides the same coherent dosimetric information as it did when the beam projection was restricted to be normal to the array plane. At one beam angle, the 2-D array appears as a plane, but with a 90 degree rotation of the radiation source, the 2-D array appears as a linear array with many lines of detectors at different depths in the array. This creates a dose information weighting problem with the detector sampling dose at depths and densities that change significantly at and near the vicinity of the beam axis as the beam rotates around the array.

There is also a need, in this 3-D dosimetry system, to measure and store the dose during specific time segments throughout the duration of the radiation delivery to the phantom, and to have no significant measurement limit on the total dose delivery. With movement of the source comes a temporal feature to the dose delivery because the position of the source is time dependent and the position of the source is a factor in the dose distribution. Any rigorous QA solution that verifies the dose delivery should do so with a number of finite "time segment" dose measurement distributions that can be compared to the desired dose distribution during any particular segment in time, or over a beam angle which is a function of time in the delivery system. Furthermore, with time segmented dose data in three dimensions and beam edge proximities to detectors, which is provided by embodiments of the present invention, it is possible to determine the source angle by ray tracing through 3-D dose distributions, and verify the source angle with the intended angle during that time segment. Without time segment data, the measured dose distribution becomes a composite of the entire dose delivery from all angles, which in itself, can be compared to the intended dose distribution, but with limited QA benefit. The composite blurs the delivery error that occurred at any given angle, just as it does in conventional IMRT QA when all fields are summed together into a composite. A current American Association of Physicists in Medicine (AAPM) task group activity (TG119) has discussed recommending against composite QA and recommending field measurement QA, but is not published at the time of this writing. Therefore, comparison of time segment measurements of dose delivery with planned dose delivery during the time segment is analogous to field QA in conventional IMRT.

There is also a need, in this 3-D dosimetry system, for a dose measurement that can localize a portion of the beam edges that occur in modulated beams and open fields. The beam edge defines the dose location and any QA solution that verifies the dose delivery preferably verifies both the magnitude of the dose and its location. This becomes particularly desirable when the source of the beam itself is moving. Each time segment preferably contains a quantifiable location of the beam during that time segment. The beam edge measurement will generally depend upon the spatial resolution of the radiation detector; therefore the "spatial frequency" of a detector is preferably high enough to sample a location in the beam edge without averaging the edge over a significant distance that would defeat the purpose of the QA localization.

There is also a need to coordinate this dose location to a spatial location defined by an imaging system, with image-guided radiotherapy (IGRT) being one such application. The patient imaging system locates anatomical landmarks (repeatably using independent markers, by way of example) that may be used to set up a patient and to monitor motion in a treatment simulator system or for image guidance during radiation therapy (IGRT). In this 3-D dosimetry system, there is a need to determine, by means of a patient imaging system, the positions of the detectors in the array. The positions can be determined by an imageable object (the detector object itself or an object whose position is known relative to the detector) that can be imaged by the patient imaging system, with spatial resolution that satisfies the localization requirements of the beam in the patient anatomy. The image location of the detector and the beam location measurement with the detector becomes a QA verification of the imaging and delivery coordinates. Such a basic concept was demonstrated and published by D. Letourneau[3], Med Phys 34(5) May 2007 "Integral Test Phantom for Dosimetric Quality Assurance of Image Guided and Intensity Modulated Stereotactic Radiotherapy." The work that Letourneau published resulted from a prototype device designed and built by Sun Nuclear Corporation with detectors in a radial plane (i.e. in the interior of the phantom). Unlike the radial plane prototype, the array geometry described for embodiments of the present invention does not require interior detectors (i.e. detectors at various radial locations). However, that does not prevent similar utilization of detectors on a 3-D surface for localization of imaging coordinates and beam location coordinates.

Film that is configured in a phantom for 3-D measurements will satisfy some needs, but not the time segment or detector imaging needs. This was nearly demonstrated in a paper by Paliwal[4] with a phantom that provided a 3-D location for film in a spiral wrap that started near the circumference and then spiraled in toward the interior of the phantom. This was commercialized by Gammex[5]. The depth of the film continuously changed depending upon the beam angle entrance; therefore the data did not result in a coherent dose measurement as later addressed in this document. As will be later described for one embodiment of the present invention satisfying this need, if film is wrapped into a cylindrical geometry that is concentric with a cylindrical phantom, then this would result in a coherent dose measurement because the beam would see the same measurement geometry, regardless of the beam angle, assuming the beam is normal to the cylinder axis.

Yet further, the 2-D arrays measure dose distributions in time segments can locate beam edges in those time segments, but cannot measure a coherent dose distribution when the source location moves with respect to array perpendicularity from one time segment to another, as will be further addressed later in this document. Such arrays could, in theory, satisfy the need to localize the imaging system to beam edges if the required design parameters satisfy the need. However, the need is rarely satisfied if by chance the features needed are in the design but the intention was not considered in the design. For example, the geometric projection of an ion chamber (on an array) that does not remain coherent with the source movement will have a spatial resolution that may change and render the localization of beam edge as not sufficient resolution to be useful. Therefore, while there may be some unintended capability to locate a beam edge in varying time segments does not mean that it has sufficient capability to satisfy the intended use. Another example is an array of detectors, as in the Delta4[6] design, that have sufficient geometric properties to satisfy beam edge localization but the measurement geometry of the array itself does not remain coherent as the source moves from one time segment to another.

SUMMARY

The present invention provides a dosimeter comprising an ionizing radiation detector array used to generally encompass a three dimensional geometric shape such as that employed as a phantom in radiation dosimetry measurements. The ionizing radiation detector array may include passive or active detectors. The active detectors in the array may comprise diodes, ionization chambers, luminescent sensors or amorphous silicon. The three dimensional geometric shape may comprise a shape defined by a closed directrix, wherein each of a plurality of detectors within the ionizing detector array is within an envelope defined by a generatrix of the directrix. The closed directrix may be in a cylinder, or a structure having a cross section described by a polygon shape. The plurality of detectors may only be positioned on or at least proximate the envelope.

Yet another embodiment may include a three dimensional dosimeter comprising a detector array having a plurality of ionizing radiation detectors therein, wherein the array forms an envelope of a closed cylinder having at least one of a circular and regular polygon shaped cross section, electronics operable with each of the plurality of detectors for measuring a detector response, and a recorder operable with the electronics for recording the response at timed intervals.

A method aspect of the invention includes measuring dose delivered by a radiation source to a phantom, wherein the method may comprise forming a phantom into a three dimensional shape, encompassing the phantom with a plurality of ionizing radiation detectors formed in an array generally having the three dimensional shape of the phantom, providing a source of radiation emitting a beam, directing the beam toward the phantom for delivering radiation thereto such that radiation passes through the phantom from one side to an opposing side thereof, wherein detectors on both the one side and the opposing side are exposed to the radiation, rotating the source of radiation around the phantom to preselected locations thereabout, and measuring a dose from all detectors at the preselected locations.

A system and method may be provided, wherein one embodiment may be provided as herein referred to as SOLI-Dose™ that may comprise a cylindrical array of imageable radiation detectors, concentric in a cylindrical phantom, and an electronics capability to simultaneously record the response of the radiation detectors at a measurement frequency sufficient to capture dose delivery at given time or gantry angle segments. The detectors may be arranged in a repeating and predictable geometric pattern for calibrating the detector array in a wide field of irradiation as described in U.S. Pat. No. 6,125,335, the disclosure of which is herein incorporated by reference in it entirety. The positions of the detectors are also predictable with respect to a source of radiation that is external to the array and moving in a manner that is predicted by the treatment planning system (TPS). With such a priori information from the TPS, an intended dose distribution at given beam angles may be compared to a measured dose from the detectors. The detector may be imaged by an image guidance system because of differences in the detector construction with respect to a phantom which is utilized in either radiographic or magnetic resonance imaging techniques. Such differences may be in atomic number in photon imaging and paramagnetic characteristics (such as barium sulfate or copper sulfate[7]) in magnetic resonance imaging.

One method of comparison of measured dose maps to intended dose maps already exists in 2-D methods used in IMRT plan comparisons, by way of example, in MapCHECK™, a distance to agreement (DTA[9, 11,]), Jursinic and Nelms[9], along with Letourneau[11] an evaluation of the DTA method and gamma[10] is defined by Low in a theoretical framework. The extension to 3-D analysis is clear mathematically, but it is dependent upon availability of a coherent or near coherent 3-D measurement geometry, such as the improvement provided by the present invention. Recent attempts to provide 3-D dosimetry that would satisfy dose delivery QA on a TomoTherapy HiArt system illustrate that the method taught in the present invention is not obvious. Sun Nuclear, Wellhofer and PTW have all addressed this need by providing a phantom that accepts their 2-D electronic detector arrays. A paper by Ann Van Esch[8] describes in detail the use of the PTW Seven29 array. In this application, the 2-D array is irradiated, rotated, then irradiated again, repeating until it is believed that sufficient density of measurements fulfill the comparison needs. This technique suffers from several aspects. By way of example, it requires several deliveries to measure the intended dose delivery distribution and which introduces reproducibility issues in the geometry of the array setups and the machine delivering the radiation, and the repeated measurement of a particular ray with the 2-D array oriented at different angles causes the measurement of that ray to be measured at different depths and distances between source to detector. This second example creates a situation where several measurements of the same beam portion will provide different results, thereby compromising the measurement coherence of the beam dosimetry. The radiation transport through the phantom also changes with beam angle, in the case of the ion chamber arrays due to the perturbation effects of the chamber cavities when they are aligned with a ray trace or orthogonal to the array plane. Furthermore, with only a few orientations of a 2-D array, there is still a significant portion of the beam that is potentially not being sampled (i.e. the entire beam that is sampled when irradiated normal to the detector plane may have portions that are not sampled by irradiating at an angle not normal to the detector plane).

Another new array that was specifically designed to address dosimetry of rotating beams is the Delta4[6] by ScandiDos. This is an array formed by intersecting two 2-D arrays at right angles to the array planes. For example, consider an array that is in the XY plane covering an area ±10 cm with respect to the origin. Then with slots on the Y axes, allow another array on the YZ plane to slide into place so that their origins intersect. Now it appears there is a 3-D array of detectors configured for 3-D measurements, but actually there are two 2-D arrays mounted orthogonally, which effectively results in a hybrid 2-D array. The projection by the radiation field sampled by the arrays is still dependent upon the beam orientation with respect to the arrays. Furthermore, the measurement of total delivered dose is not coherent from one beam segment (in time or angle) to another. Therefore, from these most recent efforts, the example embodiment of a cylindrical configuration of detectors is not the obvious detector geometry to implement for the needs for the dosimetry of rotating beams; not in design or in practice in how to manufacture, as earlier addressed in the background section of this document. The cylindrical shape detector array provides the geometry that allows coherent dose measurements as the source rotates around the cylinder axis.

One embodiment of the invention may comprise a detector array being shaped into a surface or envelope that encompasses a solid, such as a solid of revolution about an axis that is perpendicular to the beam axis. It is desirable to have the detectors located on a parametric surface that allows their position in a 3-D coordinate system to be mapped by calculation with respect to the source movement. At any beam angle (unit time), the measured dose distribution on this parametric surface is a map of the radiation flux passing through the solid. For example, if a circular field of radiation impinged on the cylinder of detectors, and the radiation source is rotated around the cylinder while the detector outputs were periodically sampled, then the radiation field pattern could be reconstructed in time and beam angle by examination of the dose intensity patterns entering and exiting the cylinder, i.e., one may plot the circle of radiation as it rotated around the cylinder. With such a map and the measured dose value at the mapped points, it is then possible to compare the TPS dose values to the measured values, either over the entire delivery or over specified time segments. If the measurement array were 2 dimensional with the same time period measurements, then one would only be able to reconstruct a planar view of the circle as it rotated, resulting in a circle that formed into an ellipse and then a straight line as the source rotated through 90 degrees. The reconstruction of the dose map, as measured with a 2-D array is not a true geometric representation of the delivered field, i.e., it cannot reproduce the circular radiation shape as can be reproduced with a cylindrical array.

The reference above to "solid" refers not necessarily to only a solid device or material without voids, but a solid geometric shape that has volume. There is no requirement to have detectors inside the volume of the phantom, as is the case with the 2-D array solutions that are described above; and there is no requirement of the contained volume to be of any particular content or uniformity. The contained volume can be filled for a specific application with specific materials providing features associated with the application, such as imaging phantom, dosimetric devices, heterogeneities for dose or imaging studies, and other obvious applications that enhance the utility of a dosimetry shell. Furthermore, the radiation flux is measured as it enters the volume and as it exits the volume, resulting in a measure of net radiation flux subtracted by the phantom along a ray tracing.

A detector array on a shell that is not continuous in curvature but formed by joining surfaces with an angle between the surfaces that still surrounds the volume (by way of example, envelope having a polygon as its cross section versus a circle as its cross section) may be applied to this dose measurement method with minor compromise to the dose measurement coherence as a function of beam angle incident on the surface of the array. One preferable shape for measurement coherence with a source that rotates in a circle around an axis, as viewed along the axis of the array that is parallel to the source rotation axis, is circular with the length of the axis defining the length of the cylinder. If not circular, a "regular polygon" (both equilateral and equiangular) will provide a useful geometry for dose measurement but with compromise to the dose measurement coherence to some extent, that extent being dependant upon the number of sides to the polygon. Coherence will improve with the number of sides. The minimum to form a shell that encloses a volume is three sides, forming an equilateral triangle; eight sides that form an octagonal surface would be more reasonable. The polygon geometry may lend itself better to particular detectors that may require rigid circuit boards, such as ion chambers. In addition, a deviation from regular polygon geometry, i.e. irregular polygon, may lend itself to any number of flat surfaces that extend around the array axis to form an enclosure of a volume that provides a 3-D array and that may be suitable, in varying degrees, for 3-D dosimetry.

One embodiment of the invention may be directed to a surface that contains a volume, and not typically to surfaces that intersect inside volumes as in the 2-D arrays. In the case of a simple rotating source constrained to move on a circle, the surfaces at either end of the cylinder are not intentionally irradiated. Therefore, there is no need to provide detectors on the cylinder end surface. However, if the source's beam axis has the freedom to move at any angle, with respect to some defined point in space, then the desirable surface shape for the detector array would be a sphere, not a cylinder. Therefore, embodiments may relate to a geometric array of detectors that measure the radiation flux impinging upon the phantom, (emitted from a source) in a coherent manner that is independent of the source's beam axis orientation to the array and the field of radiation as determined by the beam limiters. The optimum array geometry is defined by the freedom of orientation of the source's beam axis. For a source that is constrained to move in a plane while the beam is on, a suitable array is a plane that is orientated normal to the beam axis. Regardless of the location of the axis on the array, measurements of the rays remain coherent. Note that a cylindrical array may also be used in place of the plane array, if the source axis is constrained to move along the cylinder axis and not in the plane. A spherical array may be used if the source is constrained from any movement. By way of example, for a source that is constrained to rotate in a circle while the beam is on and with the beam axis directed inward toward the center of the circle, one optimum array geometry includes a cylindrical shape. For a source that is constrained to rotate on a spherical pattern while the beam is on and with the beam axis directed inward toward the center of the sphere, an optimum array geometry may be a sphere. Furthermore, an added benefit of the 3-D nature of an array is the measurement of the radiation as it enters the 3-D array and as it exits the 3-D array. By ray tracing at beam edges and finding consensus of the ray tracing, it is possible to determine the source's beam axis, thereby enabling QA of its intended orientation.

There are alternate methods of producing a solid surface array, such as cylindrical or polygonal. By way of example, one may include a flexible circuit with detectors mounted in a manner that will allow wrapping the array in a cylindrical (solid) shape (or near cylindrical circle), with means to terminate the detector signal conductor either directly to the measuring electronics on the flexible circuit or through a connector on the flexible circuit that then terminates to another circuit with the measuring electronics. A second method may comprise detectors mounted on multiple rigid circuit boards that may be mounted together such that where the circuit boards meet on one side, the opposite side meeting another circuit board at the same angle and repeating until all the circuit boards have met on two sides, and together having enclosed a volume with the ends forming a regular polygon. The rigid circuit boards would have means to terminate the detector signal conductor either directly to the measuring electronics on the rigid circuit or through a connector on the rigid circuit that then terminates to another circuit with the measuring electronics.

With regard to SOLIDose QA software applications, based on established practices of patient specific dose delivery QA, there are well established methods of dose map comparisons, as found in current 2-D array products such as MapCHECK[1] measured versus planned, that are applicable in this 3-D geometry array. These methods include dose map comparisons of total dose composite and fractional dose maps in discreet time segments (analogous to fields in conventional IMRT). By way of further example, SOLIDose™ QA methods may be used to determine source location by ray tracing for given time sequence and field shape. Given sufficient image data of the detectors on the array, the software may correlate the source coordinates to the expected source coordinates by way of beam edge data as measured by the detector and image coordinate location of the detector. The data may also be exported to other system applications that perform various QA delivery verifications. The software methods and applications are not part of this disclosure. The desirable results from these methods is made possible by the invention disclosed herein.

BRIEF DESCRIPTION OF DRAWINGS

A preferred embodiment of the invention, as well as alternate embodiments are described by way of example with reference to the accompanying drawings and photographs in which.

DESCRIPTION OF EMBODIMENTS

The present invention will now be described more fully hereinafter with reference to the accompanying drawings, in which embodiments of the invention are shown. This invention may, however, be embodied in many different forms and should not be construed as limited to the embodiments set forth herein. Rather, the embodiments herein presented are provided so that this disclosure will be thorough and complete, and will fully convey the scope of the invention to those skilled in the art.

Figure 1:
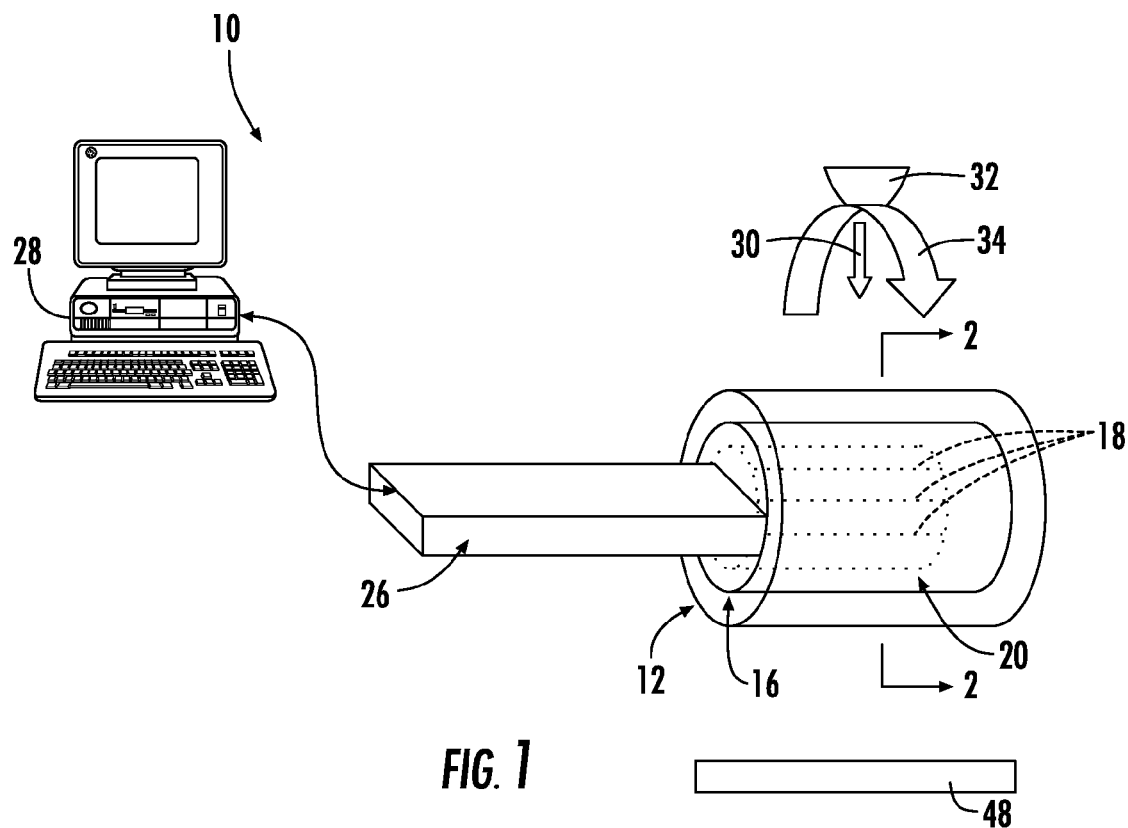
FIG. 1 is a diagrammatical illustration of a dosimetry measurement system including a detector array embedded within a cylindrical phantom according to the teachings of the present invention.
Figure 2:
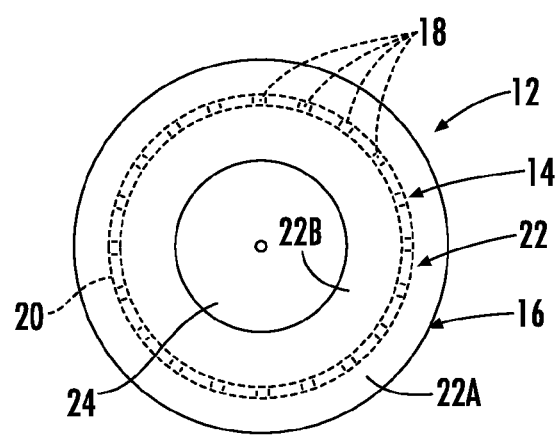
FIG. 2 is a partial cross sectional view of the phantom and array taken through lines 2-2 of FIG. 1.

With reference initially to FIGS. 1 and 2, a system 10 for measuring radiation dose according to the teachings of the present invention comprises a dosimeter 12 including an ionizing radiation detector array 14, wherein the array encompasses a three dimensional geometric shape such as the cylindrical phantom 16, herein described by way of example. The array 14 may comprise a passive detector array or an active detector array. For the embodiment herein described by way of example, the active detector array 14 comprises each detector 18 within the array 14 formed from diodes, but may also comprise ionization chambers, luminescent sensors, or amorphous silicon. In addition, while a cylindrical shape is illustrated by way of example, the dosimeter 12 may be a three dimensional geometric shape defined by a closed directrix, and wherein each of a plurality of detectors 18 within the ionizing detector array 14 is within an envelope defined by a generatrix of the directrix, as will be addressed later in this disclosure. By way of example, the closed directrix may include the cylindrical shape illustrated with reference to FIGS. 1 and 2, or any regular polygon shape, as will be addressed later in this section. Yet further, and for the embodiment of FIGS. 1 and 2, the plurality of detectors 18 is positioned only within the envelope 20, but as will come to the mind of those skilled in the art, detectors may be located at other desirable positions without departing from the essence and teachings of the present invention.

Figure 3A:
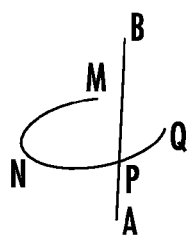
FIGS. 3A and 3B are geometric diagrams illustrating generatrix and directrix terminology and a resulting cylinder, respectively.
Figure 3B:
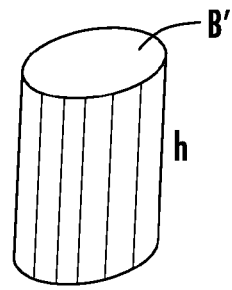
Figure 4A:
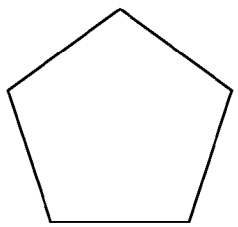
FIGS. 4A and 4B illustrate geometric shapes for regular and irregular pentagons, respectively.
Figure 4B:
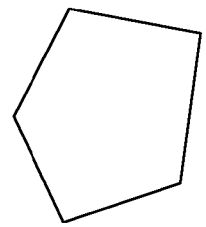
Figure 5:
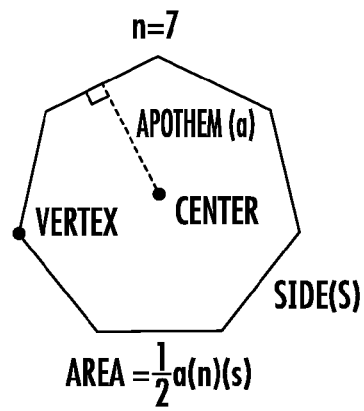
FIG. 5 is a diagrammatical illustration of terminology used in describing shapes in keeping with terminology used to describe embodiment of the present invention.

Before proceeding further with regard to features and embodiment of the present invention, and to aid the reader, the following definitions are provided:

a. Coherent=1) marked by an orderly, logical, and aesthetically consistent relation of parts; 2) logically connected, consistent; having a natural or due agreement of parts; 3) harmonious; 4) having the same property at a time and across time. Consider one particular beamlet emitted from the source at some angle from the beam axis. Now consider the measurement of this beamlet, as the source moves relative to the dosimetry array. A detector's location when the beamlet is measured determines the coherence of the measurement relative to measurements of the same beamlet at other points in time. Here it is assumed that the response of all detectors is invariant, i.e., the same measurement result, in identical measurement geometry, would occur, regardless of which detector makes the measurement.

i. For example, uniform dosimetric film forming a cylindrical geometry will provide a coherent dose measurement as the beam axis rotates on a circle around the cylinder while remaining normal to the cylinder axis. At each angle of rotation, the particular beamlet will be measured by the film at the same source to detector distance (SDD), the same angle of incidence to the film detector, the same depth in the phantom, but at a different point on the film. If the film response is invariant to location on the film, then the beamlet will be measured at each angle as if there were no beam axis or cylinder rotation, providing a coherent measurement at a time and across time as the rotation progresses.

ii. As an example of an incoherent measurement, the film forms a spiral around an axis, as in the Paliwal spiral phantom. At each angle of rotation, a particular beamlet will be measured by the film at a different SDD, at a different angle of incidence to the film detector since the radius changed, and at a different depth in the phantom. The film response may be invariant (normal to the film "plane") to location on the film, but each angle of measurement provides a unique measurement geometry for the given beamlet, i.e., the beam axis rotation provides a different view of the detector for a given beamlet across time, thus destroying the measurement coherence.

iii. The film examples provide illustration of an array with nearly a continuum of detectors, i.e., very high density. Now consider an array that has a repeating geometric pattern of detectors with inactive regions between the detector locations. For example, on the circumference of the cylinder there exists a detector at every one cm increment, and there are circumferential rows along the length of the cylinder spaced every one cm. Again, consider one particular beamlet emitted from the source at some angle from the beam axis, and again consider the measurement of this beamlet, as the source moves relative to the dosimetry array. Only at given repeating angles will this particular beamlet be measured, when one of the circumferential detectors is aligned to the beamlet, which occurs every 1 cm along the length of the circumference. At each of these given angles, the given particular beamlet will be measured by a detector positioned at the same source to detector distance (SDD), the same angle of incidence to the detector, the same depth in the phantom, but by different detectors on the circumference. If the detector's response is invariant by proper calibration in the array, then the beamlet will be measured at each angle as if there were no beam axis or cylinder rotation, thus providing a coherent measurement at a time and across time as the rotation progresses.

iv. As an example of an incoherent measurement with a repeating detector pattern, a detector array exists in a flat plane in a phantom and the plane is initially normal to the beam axis. As the source rotates in a circle around the array center, the beam axis is no longer normal to the detector plane and eventually is parallel to the plane at a 90 degree rotation. Considering again one particular beamlet, only at given non-repeating angles will this particular beamlet be measured, when one of the detectors on the plane is aligned to the beamlet, which occurs more frequently or less frequently, depending upon the beamlet angle from the beam axis. On the beam axis, the center array detector always measures the same beamlet, and parallel to the array, all detectors on the array aligned to the rotation measure the beam axis, each at different SDD and depth. Off the beam axis, when a beamlet is measured by a detector, it is at a different SDD, a different angle of incidence and a different phantom depth. The detector response may be invariant to location on the array by proper calibration, but each angle of incidence measurement provides a unique measurement geometry for the given beamlet, i.e., the beam axis rotation provides a different view of the detector for a given beamlet across time, thus destroying the measurement coherence.

v. Finally, in the above example (iii) of the repeating detector that possesses measurement coherence, the particular beamlet that is measured at repeated beam angles have a neighborhood of other beamlets that are also measured, each having their own unique but consistent SDD, angle of incidence, and phantom depth. Then at angles where these particular beamlets are not measured, there is another neighborhood of beamlets that are being measured. With a continuous rotation of the source around the cylinder, there is a near continuous measurement of beamlet neighborhoods, each measurement repeating in a coherent manner.

b. Invariant=1) a quantity or expression that is constant throughout a certain range of conditions, 2) Unaffected by a designated operation, as a transformation of coordinates, 3) unchanged by specified mathematical or physical operations or transformations c. Cylinder[12]
   i. Merriam-Webster Online Dictionary "1 a: the surface traced by a straight line moving parallel to a fixed straight line and intersecting a fixed planar closed curve b: a solid or surface bounded by a cylinder and two parallel planes cutting all its elements
   ii. Microsoft Encarta [12] "Three-dimensional geometric figure" Quoting Further . . . . A circular cylinder consists of two circular bases of equal area that are in parallel planes, and connected by a lateral surface that intersects the boundaries of the bases. More generally, a cylinder need not have circular bases, nor must a cylinder form a closed surface. If MNPQ is a curve in a plane (reference being made to FIG. 3A), and APB is a line that is not in the plane and that intersects the curve at a point P, then all lines parallel to AB and intersecting MNQ when taken together form a cylindrical surface. If the curve MNPQ is closed, the volume enclosed is a cylindrical solid. The term cylinder may therefore refer to either the solid or the surface. The line APB, or any other line of the surface that is parallel to APB, is called a generatrix or element of the cylinder, and the curve MNPQ is called a directrix or base. In a closed cylinder, all the elements taken together form the lateral surface. A closed cylinder is circular, elliptical, triangular, and so on, according to whether its directrix is a circle, ellipse, or triangle. In a right cylinder, all elements are perpendicular to the directrix; in an oblique cylinder, the elements are not perpendicular to the directrix. In general, the volume of a closed cylinder between the base and a plane parallel to it is given by B'h, in which B' is the area of the base and h is the perpendicular distance between the two parallel planes, reference being made to FIG. 3A.

d. Polygon [12], Again quoting from Microsoft Encarta [11] ... in geometry, a simple closed two-dimensional figure formed by the joining of three or more straight line segments, called sides. A figure is simple if it extends in no more than two directions from any point and closed if its starting point is the same as its endpoint. These restrictions require that the sides of a polygon not cross each other and that pairs of sides intersect at their endpoints, which are called vertices. As illustrated with reference to FIGS. 4A and 4B, all polygons have an equal number of sides and vertices, and the sum of the interior angles of a polygon with n sides is 180°×(n−2). If the sides of a polygon are of equal length and the angles are equal, the polygon is regular; otherwise it is irregular. As illustrated with reference to FIG. 5, the distance from the center of a regular polygon to a side is called its apothem. One-half the apothem times the number of sides times the length of a side provides the area of a regular polygon: Area ½ a(n)(s).

Figure 6A:
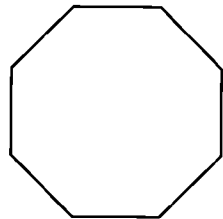
FIGS. 6A and 6B illustrate geometric shapes for convex and concave octagons, respectively.
Figure 6B:
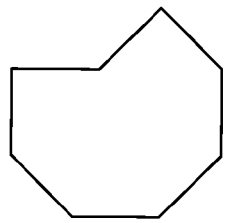

Polygons are either convex or concave, as illustrated with reference to FIGS. 6A and 6B. Every interior angle of a convex polygon is less than 180°, while at least one angle of a concave polygon is greater than 180°. An easy way to tell if a polygon is convex is to lay a ruler along each side in turn. If the ruler never juts into the inside of the polygon, the polygon is convex. If it does jut inside, however, the polygon is concave. A polygon's name reflects the number of sides it has. The best-known polygons are the triangle, which has three sides; the quadrangle, which has four sides and includes squares, rectangles, and parallelograms; the pentagon, which has five sides; the hexagon, which has six sides; the heptagon, which has seven sides; the octagon, which has eight sides; the nonagon, which has nine sides; and the decagon; which has ten sides.

e. Solid Geometry [12]
  i. Solid (geometry) [12]=three-dimensional figure along with the volume it encloses.
  ii. Solid Geometry [12]=branch of geometry that deals with the properties and measurement of geometric figures in three-dimensional space.

In the context of this document, it is clear that the solid formed by the array need not actually be a physically solid material, but that the array may be on a surface that encloses or surrounds a volume that could contain materials, cavities, and the like. For the embodiment herein presented with reference again to FIG. 2, dose measurements are made using a medium 22 surrounding the detector array 14 that provides an electron equilibrium ("buildup") for each detector 18 in the radiation field being measured. It may be sufficient for the array 14 on a three dimensional cylindrical surface to be surrounded by media on either side (external medium 22A and internal medium 22B) of the cylindrical array 14, and still have a cavity 24 in the volume of the cylindrical array, as herein presented by way of example.

With reference again to FIG. 1, one embodiment of the invention, herein referred to as a SOLIDose™ system 10 comprises the cylindrical array 14 of imageable radiation detectors 18 on an array that is concentric in the cylindrical phantom 16. The system further comprises electronics capable of simultaneously recording a response of the detectors 18, herein using a processor 28, at a measurement frequency sufficient to capture dose delivery from a beam 30 at given time or angle of a gantry 32 during preselected dose delivery segments 34. For the embodiment herein described by way of example, the detectors 18 are arranged in a repeating and predictable geometric pattern, making it possible to calibrate the detector array in a wide field of irradiation as described in U.S. Pat. No. 6,125,335.

As illustrated with reference to FIG. 7, the cylindrical array 14 is formed with a Kapton flexible circuit 36, approximately 20 cm in diameter and 3 cm in length. The radiation detectors 18 mounted on Kapton pads 38 are diodes with a measurement area 0.8 mm×0.8 mm and a construction with metal contacts allowing x-ray imaging and/or paramagnetic characteristics that allow MRI imaging. The phantom 16 may be made of a plastic material, close to water density, with a 2.5 cm thickness over the detectors 18 and 2 cm below the detectors 18 resulting in a shape with 25 cm outer diameter and 16 cm inner diameter. With reference again to FIG. 1 and now to FIG. 8, the measurement electronics 26 is composed of a multi-electrometer application specific integrated circuit (ASIC) with a measurement time of 50 ms and unlimited in charge measurement from the detectors, along with associated digital circuits that communicate and transmit data to a PC.

Figure 9:
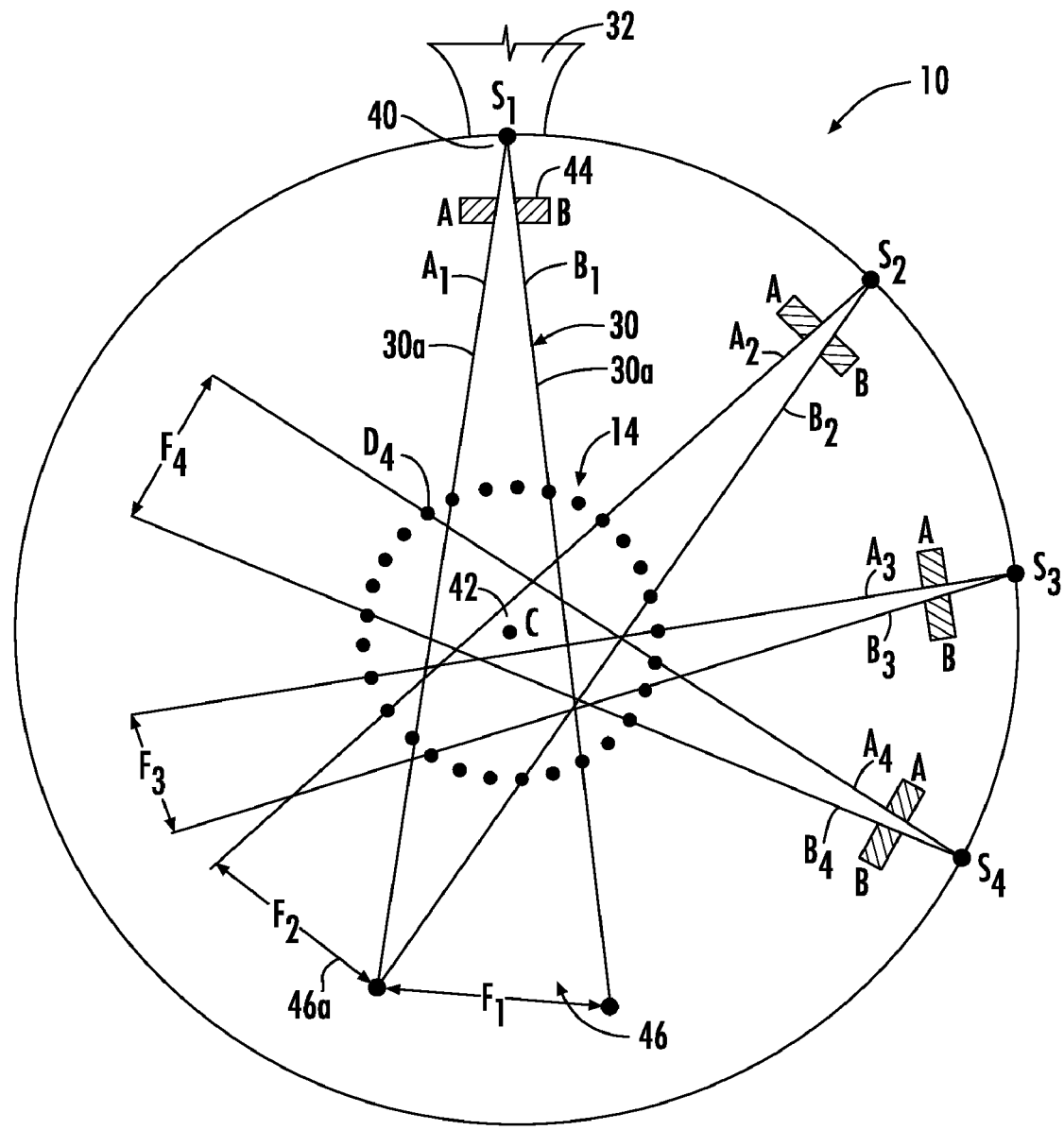
FIG. 9 is a diagrammatical axial view illustrating a detector array within a radiation field provided by a rotatable radiation source and leaf pairs for controlling dose delivery at preselected locations around the array.

Without illustrating the detailed electronics 26 of FIG. 1, an axial view of the system 10 is illustrated in the line drawing of FIG. 9, wherein the radiation source S 40 from the gantry 32 is rotating around a center C 42, with 4 different time segments indicated as examples at source positions $S_1, S_2, S_3, S_4$, The cylindrical detector array 14 also illustrated as $D_n$ is also shown and is concentric to the rotation of the source 40. The illustration is not drawn to scale for clarity. Only one radial array 14 of detectors 18 (i.e. one pass around the cylinder circumference) is shown. The radiation beam 30 from the source 40 is limited by blocks or leaf pairs 44 (A and B). A beam edge 30a for each position is shown as $(A_1, B_1), (A_2, B_2), (A_3, B_3), (A_4, B_4)$. One can think of this illustration as sampling the radiation fields defined by one leaf pair of an MLC leaf bank of a LINAC. The field 46 of radiation passing through each leaf pair is passing through the cylindrical array $D_n$ 14 and designated as $F_1, F_2, F_3, F_4$. It is observed that the field width 46a changes as the source 40 rotates. The independent movement of leaves in each leaf pair 44 allows the placement of radiation virtually anywhere allowed by the range of movement of the leaves, including fields that do not pass through the center as herein illustrated for $F_3$. Each dot seen on the cylindrical array 14 $D_n$ represents a radiation detector 18. Notice how each beam edge 30a $(A_2, B_2), (A_3, B_3), (A_4, B_4)$ pass in close proximity to a radiation detector 18, how some detectors 18 are well inside the field of radiation, and how others are well outside the field of radiation. Regardless of the orientation of the source 40, the field of radiation 46 enters the cylindrical array 14 $D_n$, passing near some detectors 18 and exits the cylindrical array $D_n$ while passing near other detectors. With a well ordered array geometry, and with a prior knowledge of the penumbra transfer function of the detector response to the beam edge shape caused by the leaf end, it is possible to re-construct the source position for a measured field of radiation.

Furthermore, an imaging system 48, as diagrammatically illustrated with reference again to FIG. 1, performing imaging analysis of the detector 18 locations provides a data set that enables the intended field position to be compared to the measured field position. The electronics records information generated by the ionizing radiation detector array 14 in response to radiation delivery by the source 40 of radiation. By way of example, the recording may provide a composite measurement of the radiation delivery or a sequence of measurements of the radiation delivery as desired. Yet further, the sequence of measurements may be based on time segments of radiation incidence or angle segments of radiation incidence, or both as desired. The processor provides means for analyzing a location of an edge of the beam formed by a position of the beam leaf pairs 44. As indicated, a position of each detector 18 within the ionizing radiation detector array 14 is imageable using the patient imaging system 48. From the imaged detector positions and a corresponding location of the beam edge, the position correspondence between a reference frame of an imaging machine and a reference frame of the radiation source may be analyzed. A measured composite dose map may then be compared to a planned dose map for the array 14. Yet further, the measured dose map in one or more sequences may be compared to corresponding dose maps of planned sequences on a preselected array geometry. An angle of incidence of the source of radiation to the array may also be analyzed.

As desired, the imaging can occur prior to delivery with a "simulator" or during delivery with image guided radiotherapy. Furthermore, a treatment planning system (TPS) calculating an intended 3-D dose map, at each field position, provides a data set that enables the intended dose distribution in the field to be compared to the measured dose points in the field, using the cylindrical detector array. The dose measurement by the detectors in the field is a direct measurement of the radiation dose delivery, as it enters the cylindrical array and as it exits the cylindrical array. The difference in comparison can be used to calculate the error and subsequent correction factor that can be applied to the intended 3-D dose map, resulting in a corrected 3-D dose map of the radiation delivery.

Figure 10:
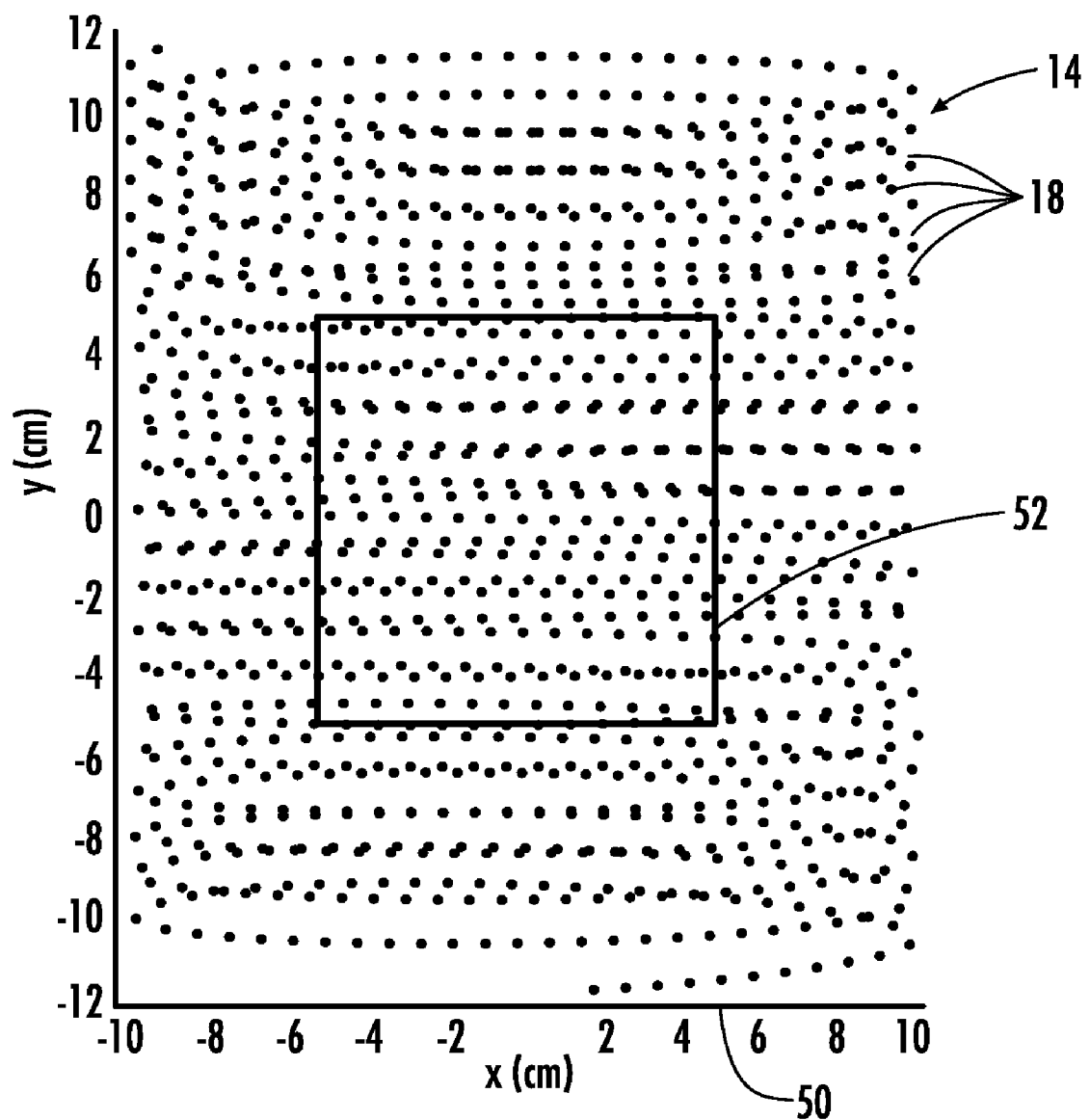
FIG. 10 is a "beams eye view" (BEV) of a cylindrical array of detectors.

By way of further illustrating and discussion, reference is now made to FIG. 10, wherein a "beams eye" view (BEV) of the cylindrical array 14 of detectors 18 is illustrated. This is a mapping of the detectors 18 onto a plane 50 at the axis of rotation and normal to the beam axis. Distortion of the uniform detector grid on the cylindrical geometry is caused by the ray tracing from the source to the detector and ray trace intersection on the 2-D plane. When the source 40 is moved by rotation around the axis of the cylinder, the BEV map will change as well. This gives the appearance of a scattered distribution of detectors 18, in part due to the 3-D geometry being projected to two dimensions with ray tracing from a single point outside the cylinder. The square 52 in the center represents a 10×10 cm field, a common reference geometry used by medical radiation physicists. The MapCHECK™ 2-D device made by Sun Nuclear provides 221 detectors in its 10×10 geometry, by way of example. The pattern for the array 14 in FIG. 10 contains approximately 220 detectors 18 in the same projected geometry.

Figure 11:
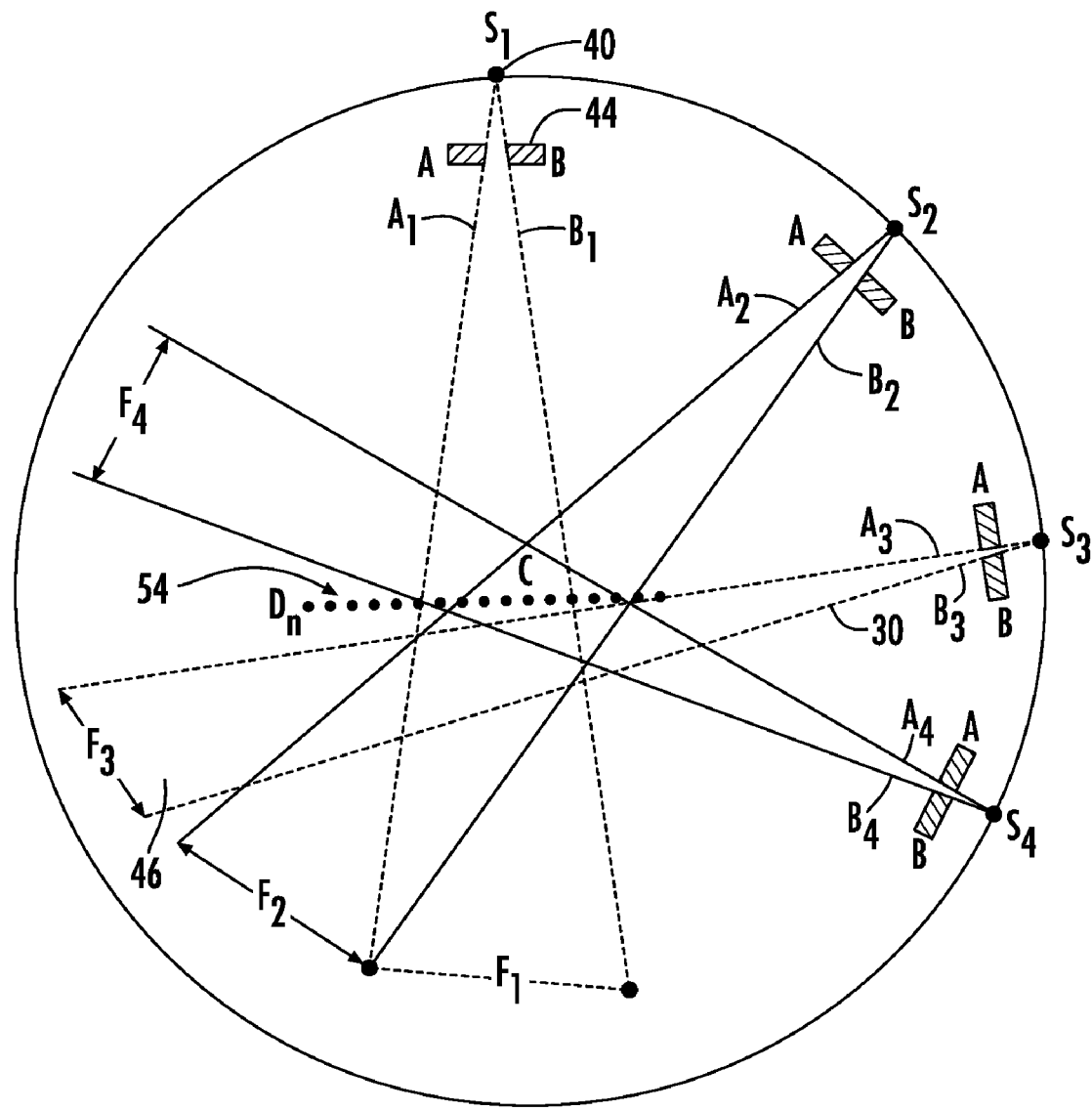
FIG. 11 is a diagrammatical illustration of a 2-D detector plane in a geometry illustrated with reference to FIG. 9 for one cylinder application.

By way of further example of assessing the efficacy of the 3-D geometry of the cylinder as applied to rotating sources, reference is made to FIG. 11 illustrating a 2-D detector plane 54 in the same geometry as used in FIG. 9 with the cylinder application. It becomes clear that the 2-D plane 54 is inadequate for measurement of the field 46 ($F_3$). Only the edge of the beam 30 of $A_3$ is measured, and such a measurement is not sufficient for accurately measuring a dose. Geometries can result in real applications where the beam 30 will miss the 2-D array entirely. Furthermore, the BEV detector density of a 2-D array, in a rotating beam, changes from a low density when the array is normal to the beam axis, to a very high density as the beam axis approaches a parallel direction to the array plane. This density change is accompanied by a depth change in the phantom 16. When these two characteristics are inherent in the dose measurement that is to be compared to an intended dose map from the planning system, the weighting of dose measurements at various location in the dose map changes as a function of source location, rendering an incoherent dose comparison. For example, at a parallel alignment of array and beam axis, there may be perfect agreement, but with the array normal to the beam axis, there may be 80 percent agreement. The parallel measurement will skew the statistics in favor of success due to its equal weighting even though the measurement occurred in a small fraction of the field, outside of which are unknown errors.

As above addressed, one embodiment of the invention may comprise ion chambers instead of diodes for each or selected detectors 18. The ion chamber collector electrodes may be part of the flexible circuit 36 that is wrapped around the plastic cylinder 16, with the electrodes aligned to cavities in the plastic cylinder with the cavity surface being conductive, but electrically isolated from the collectors with a voltage bias that will cause ions to be collected. Such an ionization chamber provides another embodiment of the radiation detector. The cavities could be either in the cylinder on which the flexible circuit is wrapped, or in the cylinder which is used to form the outer shell of the cylinder. The collectors may be on either one side or the other as required by proper alignment to the cavity with the collector in the cavity.

By way of example of success of the present invention, the array 14 earlier described with reference to FIG. 7, and manufactured by Sun Nuclear Corporation, has been successfully tested in a clinical radiation therapy environment. A manuscript is in the review process for publication in Medical Physics. The name given to this device is the "prototype ArcCHECK" developed by Sun Nuclear Corporation; it is a cylindrical detector array that is embedded in a cylindrical PMMA (polymethyl methacrylate) phantom whose physical dimensions are 15 cm inner diameter, 25 cm outer diameter, and a nominal length of 13.2 cm. The internal detector array 14 in the phantom 16 is composed of diode detectors 18 that are mounted on the Kapton flex circuit 36 which is wrapped around an inner cylindrical circle, forming a 19.7 cm diameter detector array. The nominal build-up thicknesses are 2.63 cm outer wall and 2.37 cm inner wall. With continued reference to FIG. 7, the phantom 16 itself is split into two cylinders, internal medium 22B and external medium 22A, where the external at 13.7 cm length, is split into two half cylinders that are clamped around the flex circuit formed onto the internal phantom cylindrical medium of 12.7 cm length.

Figure 7:
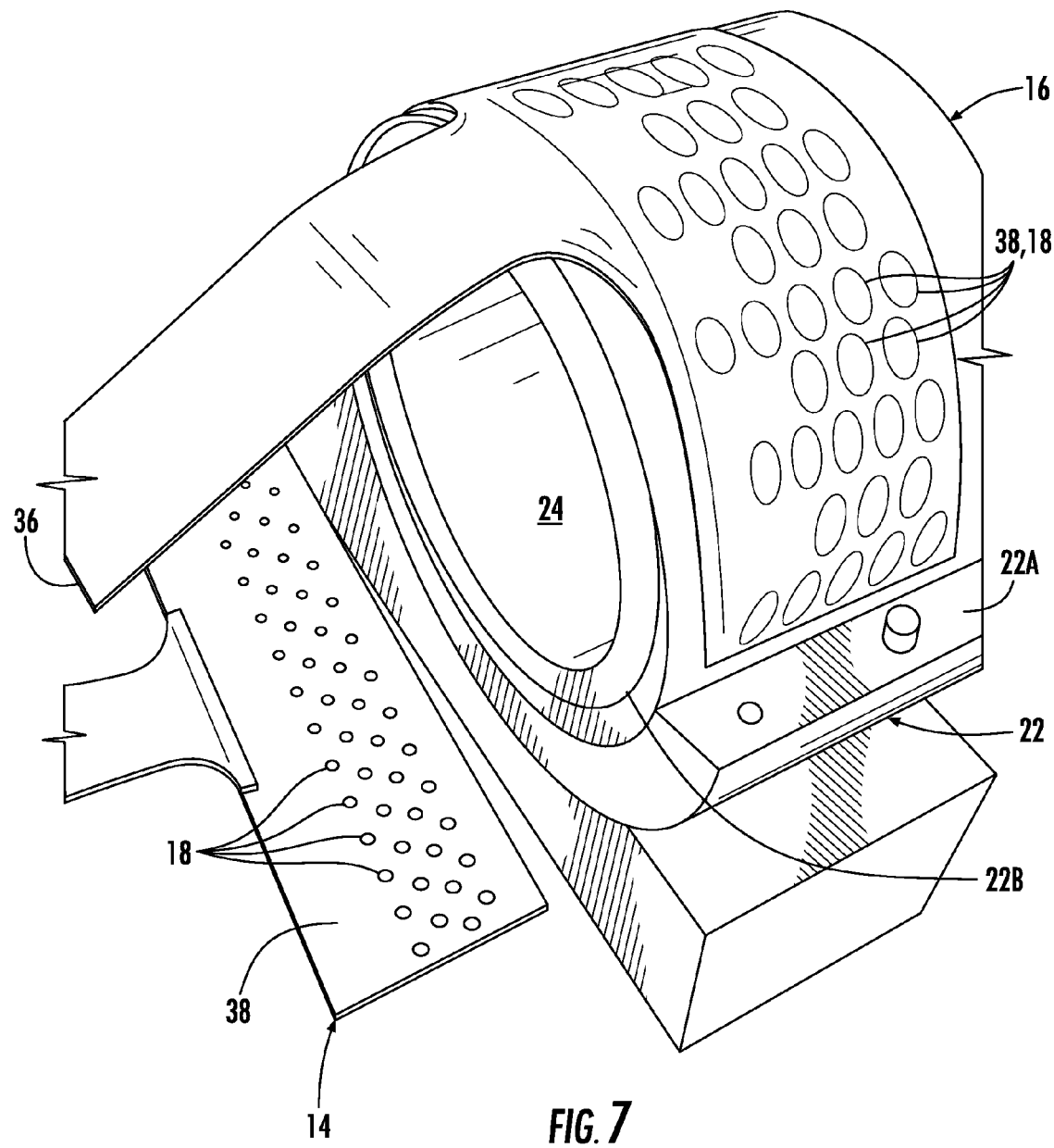
FIG. 7 is a partial perspective view of a detector array secured within a phantom.

With continued reference to FIG. 7, a zig-zag detector pattern is shown along with the Kapton circuit 36 and PMMA phantom 16. The inner surfaces of the phantom that are adjacent to the detector circuit array are conductive to prevent outside electrical interference. The detectors 18 are mounted on the flex circuit side that is in contact with the inner cylinder and located in recesses in the inner cylinder surface. There are 31 detectors located on the circumference of 62 cm, resulting in 2 cm spacing along the circumference. There are four circumference detector rings, spaced 1 cm apart and rotated 1 cm with respect to neighbor rings. This results in the zig-zag pattern or alternating detectors 18 offset in adjacent rows when viewing the flex circuit on a flat plane. In a beams eye view without divergence, the entrance detectors appear between the exit detectors in the same ring, thus creating the illusion a 1 cm detector grid. However, including beam divergence and projecting the detector geometry onto the mid plane of the cylinder (isocentric plane of the linac), this uniform grid is no longer apparent, except in the beam center.

The shielded flex circuit 36 exits the phantom 16 and is terminated inside a shielded electronics assembly. Each detector 18 is connected to a dedicated amplifier in a custom application specific integrated circuit (ASIC), as illustrated with reference again to FIG. 8. The custom ASIC was developed by Sun Nuclear Corporation for the specific purpose of radiation detection. It has 64 high impedance amplifiers whose analog outputs are converted to digital signals and are simultaneously latched and then read by a microcontroller every 50 milliseconds. Linac pulse synchronization is also allowed. The digital data is then communicated to the processor 28 such as in a computer application, running on a PC Windows operating system. The digital data is mapped to the corresponding detector locations.

Figure 8:
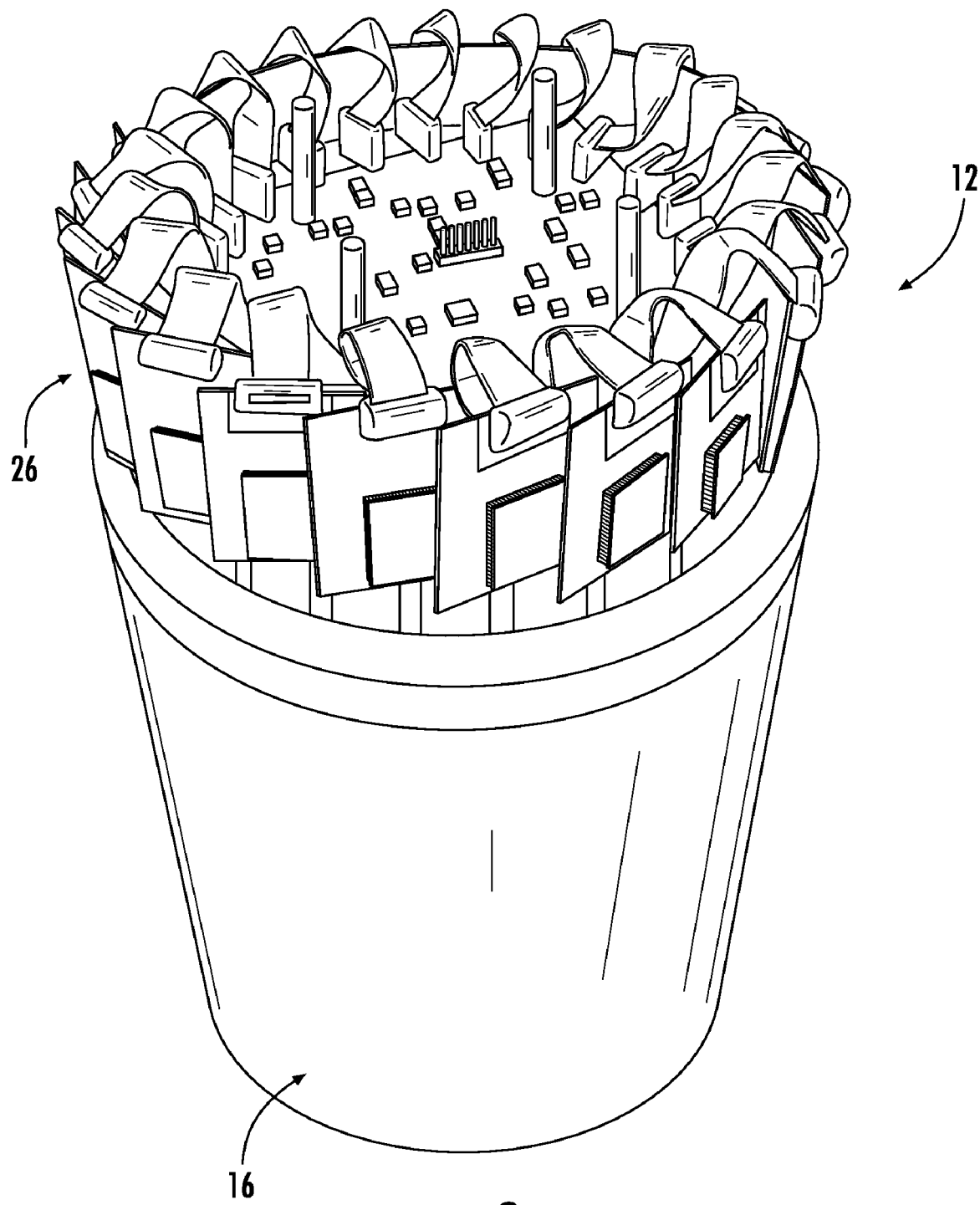
FIG. 8 is a perspective view of one embodiment of a dosimeter in keeping with the teachings of the present invention.

With continued reference to FIG. 8, a commercial dosimeter 12 referred to as ArcCHECK™ is presented as developed by Sun Nuclear Corporation and includes an extended geometry with an array diameter of 21 cm. The detector array 14 spirals along the length cylinder's generatrix with a detector spacing of 1 cm along the circumference and a 1 cm spacing of the spiraled circumferential arrays. The array length will extend 21 cm along the cylinder. The Kapton flex circuit 36 earlier described is not used as above described, instead the detectors 18 are mounted on 22 rigid circuit boards, each of which form a generatrix of the cylinder, resulting in a closed cylindrical regular polygon solid shape and 1386 diode detectors in the array.

The performance of the dosimetric phantom employing the detector array for defining the desired geometry has been assessed for the QA of linear accelerators capable of VMAT delivery. A calibration method taking into account the diode variation in radiation sensitivity as a function of gantry angle was implemented. The dosimeter system demonstrated the feasibility of VMAT QA using diodes with good reproducibility and acceptable angular response. The phantom offered sufficient sensitivity for the detection of small gantry rotation offset and scaling errors as well as phantom setup errors. Yet further, the dosimeter system demonstrated the discretization effect of the number of CPs used in the TPS to simulate a continuous arc. Based on test results, the dosimeter system according to the teachings of the present invention was shown to be desirable for patient-specific QA of VMAT plans and provides an effective tool in the routine QA and commissioning of treatment machines capable of VMAT delivery and CBCT image guidance. This testimonial is reported by Daniel Letourneau of the Radiation Medicine Program, Princess Margaret Hospital, Toronto, ON, Canada, et al. as reported in a publication titled: "Novel Dosimetric Phantom for Quality Assurance of Volumetric Modulated Arc Therapy."

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the claims supported by this disclosure.

TECHNICAL REFERENCES

1. "MapCHECK" by Sun Nuclear Corp, Melbourne Fla.; "MatriXX" by IBA (Scanditronix-Wellhofer), Schwarzenbruck Germany; "Seven29" by PTW, Freiburg Germany
2. "Rapid Arc" by Varian, _____ CA; "HI-ART" by TomoTherapy, Madison Wis.; "VMAT" by Elekta, Crawley UK, "Single Arc Therapy (SAT)" by Siemen, Germany; "CyberKnife" by Accuray, Sunnyvale, Calif.; "Renaissance" by Viewray, Cleveland Ohio
3. D. Letourneau, H. Keller, M. B. Sharpe and D. A. Jaffray, "Integral test phantom for dosimetric quality assurance of image guided and intensity modulated stereotactic radiotherapy," Med. Phys. 34(5) May 2007
4. B. Paliwal, W. A. Tome, S. Richardson, and T. Rockwell Mackie, "A spiral phantom for IMRT and tomotherapy treatment delivery verification," Med. Phys. 27, 2503-2507 (2000). [ISI][MEDLINE]
5. Gammex RMI. Madison Wis., designed the 469 IMRT phantom based on research conducted by the University of Wisconsin medical physics researchers cited in 3.
6. "Delta4" by ScandiDos, Uppsala, Sweden
7. U.S. Pat. No. 4,777,442 to Rosenthal
8. A. Van Esch, C. Clermont, M. Devillers, M. Iori, and D. P. Huyskens, "On-line quality assurance of rotational radiotherapy treatment delivery by means of a 2-D ion chamber array and the Octavious phantom," Med. Phys. 34, 3825-3837 (2007)
9. Paul A. Jursinic, Ben E. Nelms, "A 2-D diode array and analysis software for verification of intensity modulated radiation therapy delivery Med. Phys., 30(5) p 870 2003,
10. D. A. Low, W. B. Harms, S. Mutic, and J. A. Purdy, "A technique for the quantitative evaluation of dose distributions," Med. Phys. 25, 656-661 (1998)
11. Daniel Létourneau, Misbah Gulam, Di Yan, Mark Oldham and John W. Wong, "Evaluation of a 2D diode array for IMRT quality assurance", Science Direct, 70(2) p 199-206 2004
12. "Cylinder,", "Polygon", "Solid Geometry", Microsoft Encarta Online Encyclopedia 2008 (http://encarta.msn.com © 1997-2008 Microsoft Corp)

That which is claimed is:

1. A dosimeter comprising an ionizing radiation detector array, the array generally encompassing a three dimensional geometric shape, wherein detectors within the array provide a generally coherent dose measurement independent of a radiation source beam orientation to the array.

2. The dosimeter of claim 1, wherein the ionizing radiation detector array comprises at least one of a passive detector array and an active detector array.

3. The dosimeter of claim 2, wherein the active detector array comprises at least one of diodes, ionization chambers, luminescent sensors and amorphous silicon.

4. The dosimeter of claim 1, further comprising a phantom formed as the three dimensional geometric shape, wherein the ionizing detector array is formed with the phantom.

5. The dosimeter of claim 1, wherein the three dimensional geometric shape comprises a shape defined by a closed directrix, and wherein each of a plurality of detectors within the ionizing detector array is within an envelope defined by a generatrix of the directrix.

6. The dosimeter of claim 5, wherein the closed directrix comprises at least one of a cylindrical shape and a regular polygon shape.

7. The dosimeter of claim 5, wherein the plurality of detectors is positioned only on or at least proximate the envelope.

8. The dosimeter of claim 1, further comprising electronic means for recording information generated by the ionizing radiation detector array in response to a radiation delivery by a source of radiation.

9. The dosimeter of claim 8, wherein the recording provides at least one of a composite measurement of the radiation delivery and a sequence of measurements of the radiation delivery.

10. The dosimeter of claim 9, wherein the sequence of measurements is based on at least one of time segments of radiation incidence and angle segments of radiation incidence.

11. The dosimeter of claim 10, wherein the source of radiation is provided by a radiation beam, and wherein the dosimeter further comprises means to analyze, from the recorded measurements, a location of an edge of the beam, the edge of the beam formed by a position of a beam limiter.

12. The dosimeter of claims 11, wherein a position of each detector within the ionizing radiation detector array is imageable using a patient imaging system.

13. The dosimeter of claim 12, further comprising means to analyze, from the imaged detector positions and a corresponding location of the beam edge, the position correspondence between a reference frame of an imaging machine and a reference frame of the radiation source.

14. The dosimeter of claim 13, further comprising means to compare a measured composite dose map to a planned dose map for the array.

15. The dosimeter of claim 14, further comprising means to compare the measured dose map in one or more sequences to the corresponding dose maps of planned sequences on the array geometry.

16. The dosimeter of claim 8, further comprising means to analyze, from the recorded measurement, an angle of incidence of the source of radiation to the array.

17. A three dimensional dosimeter comprising:
a detector array having a plurality of ionizing radiation detectors therein, wherein the array forms an envelope of a closed cylinder having at least one of a circular and polygon shaped cross section, and wherein detectors within the array provide a generally coherent dose measurement independent of ,a radiation source beam orientation to the array;
electronics operable with each of the plurality of detectors for measuring a detector response; and
a recorder operable with the electronics for recording the response at timed intervals.

18. The dosimeter of claim 17, further comprising means for comparing a measured composite dose map to a planned dose map for the array.

19. The dosimeter of claim 17, further comprising means for comparing a measured dose map in one or more sequences to a corresponding dose map of planned sequences on the array.

20. The dosimeter of claim 17, further comprising a phantom, wherein the detector array is embedded within the phantom.

21. The dosimeter of claim 20, wherein the phantom includes a cavity therein, and wherein the cavity is within the array.

22. The dosimeter of claim 17, wherein the polygon shaped cross section is a regular polygon shaped cross section.

23. A method of measuring dose delivered by a radiation source to a phantom, the method comprising:
forming a phantom into a three dimensional shape;
encompassing the phantom with a plurality of ionizing radiation detectors formed in an array generally having the three dimensional shape of the phantom, wherein detectors within the array provide a generally coherent dose measurement independent of a radiation source beam orientation to the array;
providing a source of radiation emitting a radiation source beam;
directing the beam toward the phantom for delivering radiation thereto such that radiation passes through the phantom from one side to an opposing side thereof, wherein detectors on both the one side and the opposing side are exposed to the radiation;
rotating the source of radiation around the phantom to preselected locations thereabout; and
measuring a dose from all detectors at the preselected locations.

24. The method according to claim 23, further comprising recording the dose generated by the ionizing radiation detector array in response to the radiation delivery.

25. The method according to claim 24, wherein the recording provides a composite dose of the radiation delivery and a sequencing of dose measurements of the radiation delivery.

26. The method according to claim 25, further comprising comparing the measured composite dose to a planned dose for the plurality of detectors.

27. The method according to claim 25, wherein the sequencing of measurements is based on at least one of segmenting a time of radiation incidence and segmenting angles of radiation incidence.

28. The method according to claim 23, further comprising placing leaf pairs at the preselected locations for defining a beam width and analyzing a location of an edge of the beam.

29. The method according to claim 28, further comprising imaging the plurality of detectors using a patient imaging system for identifying a position of each detector therein.

30. The method according to claim 29, from the imaged detector positions and a corresponding location of the beam edge, comparing the position between a reference frame of an imaging machine and a reference frame of the radiation source.

31. The method according to claim 23, further comprising comparing the measured dose at one or more locations to a corresponding dose of planned dose sequences on the phantom at the one or more locations.

32. The method according to claim 23, wherein the three dimensional shape forming comprises forming the shape with a closed directrix, and the encompassing includes positioning each of a plurality of detectors within an envelope defined by a generatrix of the directrix.

33. The method according to claim 32, wherein the closed directrix comprises at least one of a cylindrical shape and a regular polygon shape.

34. The method according to claim 32, wherein the encompassing of the plurality of detectors includes positioning the plurality of detectors only on or proximate the envelope.

* * * * *